(12) United States Patent
Nakagawa (10) Patent No.: US 10,488,268 B2
(45) Date of Patent: Nov. 26, 2019

(54) TEMPERATURE DIFFERENCE MEASURING APPARATUS

(71) Applicant: OMRON Corporation, Kyoto-shi, Kyoto (JP)

(72) Inventor: Shinya Nakagawa, Omihachiman (JP)

(73) Assignee: OMRON Corporation, Kyoto-shi (JP)

( * ) Notice: Subject to any disclaimer, the term of this patent is extended or adjusted under 35 U.S.C. 154(b) by 254 days.

(21) Appl. No.: 15/680,500

(22) Filed: Aug. 18, 2017

(65) Prior Publication Data

US 2017/0343421 A1    Nov. 30, 2017

Related U.S. Application Data

(63) Continuation of application No. PCT/JP2016/055445, filed on Feb. 24, 2016.

(30) Foreign Application Priority Data

Mar. 12, 2015   (JP) .................................. 2015-049431

(51) Int. Cl.
*G01K 7/02*    (2006.01)
*G01K 3/14*    (2006.01)
(Continued)

(52) U.S. Cl.
CPC .................. *G01K 3/14* (2013.01); *A61B 5/01* (2013.01); *G01K 1/18* (2013.01); *G01K 7/00* (2013.01);
(Continued)

(58) Field of Classification Search
CPC ... H01L 2924/1461; G01K 7/028; G01K 7/02
(Continued)

(56) References Cited

U.S. PATENT DOCUMENTS 6,100,463 A  *  8/2000  Ladd ....................... H01L 35/34
                                                        136/201
6,203,194 B1    3/2001  Beerwerth et al.
(Continued)

FOREIGN PATENT DOCUMENTS

CN         1250519 A       4/2000
CN       101603933 A      12/2009
(Continued)

OTHER PUBLICATIONS

English translation of Written Opinion of PCT/JP2016/055445 dated Mar. 22, 2016.
(Continued)

*Primary Examiner* — Gail Kaplan Verbitsky
(74) *Attorney, Agent, or Firm* — Metrolex IP Law Group, PLLC (57) ABSTRACT

A temperature difference measuring apparatus includes: a bottomed tubular package in which a top face side is opened; a MEMS device disposed on an inner bottom face of the package, the MEMS device comprising at least one thermopile that measures a temperature difference, which is generated in the MEMS device by inflow heat through a bottom of the package; and a heat quantity increasing unit configured to increase a heat quantity flowing out from the MEMS device onto the top face side of the bottomed tubular package.

9 Claims, 7 Drawing Sheets

(51) Int. Cl.
*A61B 5/01* (2006.01)
*G01K 1/18* (2006.01)
*G01K 7/00* (2006.01)
*G01K 17/00* (2006.01)
*G01K 13/00* (2006.01)

(52) U.S. Cl.
CPC ........... *G01K 7/028* (2013.01); *G01K 13/002* (2013.01); *G01K 17/00* (2013.01); *A61B 2562/028* (2013.01); *A61B 2562/0271* (2013.01); *H01L 2924/1461* (2013.01)

(58) Field of Classification Search
USPC ......... 374/170, 178, 179, 110, 112, 113, 137
See application file for complete search history.

(56) References Cited

U.S. PATENT DOCUMENTS

| | | | | |
|---|---|---|---|---|
| 9,222,837 | B2* | 12/2015 | Mao | G01J 5/022 |
| 10,168,211 | B1* | 1/2019 | Emadi | G01J 3/108 |
| 2008/0262773 | A1 | 10/2008 | Howell | |
| 2009/0310644 | A1 | 12/2009 | Van De Kerkhof et al. | |
| 2014/0010263 | A1 | 1/2014 | Hosoi et al. | |
| 2014/0204976 | A1* | 7/2014 | Peroulis | G01K 7/34 374/184 |
| 2014/0233601 | A1 | 8/2014 | Van De Kerkhof et al. | |
| 2015/0010040 | A1 | 1/2015 | Ito et al. | |
| 2015/0168221 | A1* | 6/2015 | Mao | G01J 5/022 257/467 |
| 2017/0167926 | A1 | 6/2017 | Van De Kerkhof et al. | |
| 2017/0238107 | A1* | 8/2017 | Walther | B81C 1/00158 381/58 |

FOREIGN PATENT DOCUMENTS

| | | |
|---|---|---|
| CN | 103542958 A | 1/2014 |
| JP | 2002-372464 A | 12/2002 |
| JP | 2007-212407 A | 8/2007 |
| WO | 2013/141153 A1 | 3/2016 |

OTHER PUBLICATIONS

Chinese Office Action dated Nov. 26, 2018 in a counterpart Chinese Patent application.
International Search Report of PCT/JP2016/055445 dated Mar. 22, 2016.

* cited by examiner

Fig. 10B

TEMPERATURE DIFFERENCE MEASURING APPARATUS

CROSS REFERENCE TO RELATED APPLICATIONS

This application is a continuation application of International Application No. PCT/JP2016/055445, filed on Feb. 24, 2016, which claims priority based on the Article 8 of Patent Cooperation Treaty from prior Japanese Patent Application No. 2015-049431, filed on Mar. 12, 2015, the entire contents of which are incorporated herein by reference.

TECHNICAL FIELD

The disclosure relates to a temperature difference measuring apparatus.

BACKGROUND ART

Figure 10A:
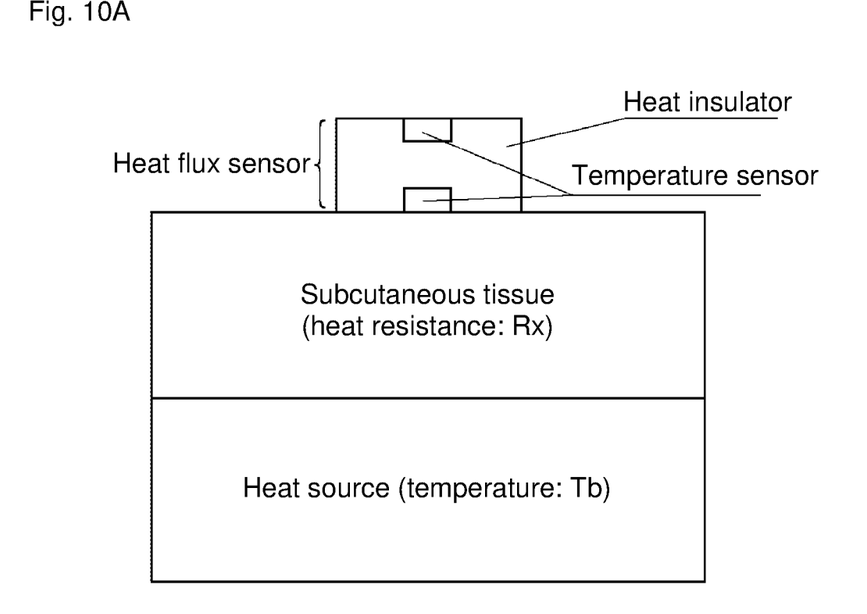
FIG. 10A is an explanatory view illustrating a sensor module used to measure (calculate) a core body temperature, the sensor module including one heat flux sensor.
Figure 10B:
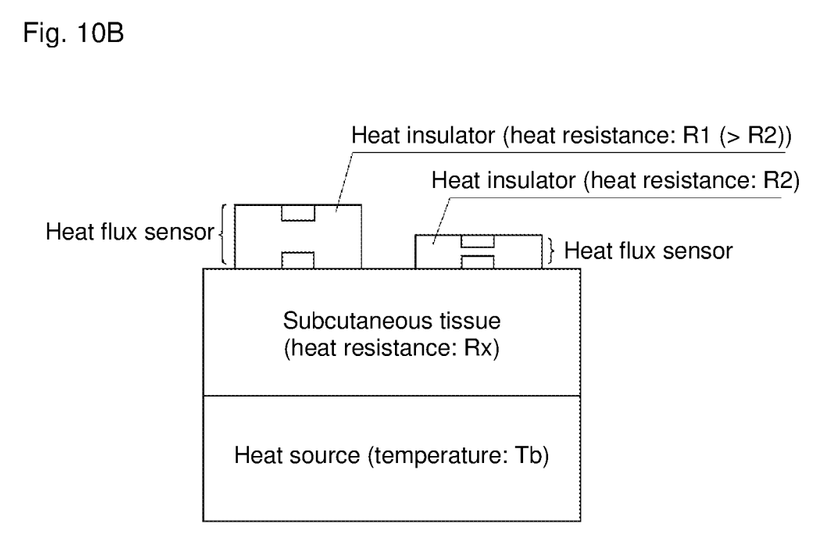
FIG. 10B is an explanatory view illustrating a sensor module used to measure (calculate) a core body temperature, the sensor module including two heat flux sensors.

Conventionally, a method in which a sensor module having a configuration in FIG. 10A is used (for example, see Patent Document 1) and a method in which a sensor module having a configuration in FIG. 10B is used (for example, see Patent Document 2) are known as a method for detecting a heat flow flowing out from a body surface and measuring (calculating) a core body temperature from a detection result.

For use of one sensor module in FIG. 10A, namely, a heat flux sensor in which temperature sensor is attached to each of top and bottom faces of a heat insulator, a core body temperature Tb is calculated using the following equation (1) from a temperature Ta measured with the temperature sensor on the top side of the heat insulator and a temperature Tt measured with the temperature sensor on the bottom side of the heat insulator.

$$Tb = (Tt-Ta)Rx/R1 + Tt \quad (1)$$

Where R1 and Rx are a heat resistance of a heat insulator and a heat resistance of a subcutaneous tissue, respectively.

In the internal temperature calculating method in which the sensor module in FIG. 10A is used, basically fixed values are used as the heat resistances R1 and Rx. However, because the heat resistance Rx depends on a location or an individual, a measurement error is included in the core body temperature Tb, which is calculated from the equation (1) using the fixed value as the heat resistance Rx, according to a difference between the heat resistance Rx used and the actual heat resistance Rx. Therefore, sometimes time changes of the temperatures Tt and Ta are measured, and the heat resistance Rx is calculated from the measurement result (see Patent Document 1).

In the case that an internal temperature is calculated with a sensor module in FIG. 10B, a temperature difference expressing a heat flux from the body surface is measured with each of two heat flux sensors having different heat resistances of the heat insulators. The following two equations can be obtained when the temperature difference is measured with the two heat flux sensors having different heat resistances of the heat insulators.

$$Tb = (Tt-Ta)Rx/R1 + Tt \quad (2)$$

$$Tb = (Tt'-Ta')Rx/R2 + Tt' \quad (3)$$

Where R1 and R2 (<R1) are heat resistances of heat insulators of the heat flux sensors as illustrated in FIG. 10B. Ta and Tt are temperatures measured with the temperature sensors on the top and bottom sides of the left heat flux sensor (a heat flux sensor in which a heat insulator having a heat resistance R1 is used) in FIG. 10B. Ta' and Tt' are temperatures measured with the temperature sensors on the top and bottom sides of the right heat flux sensor (a heat flux sensor in which a heat insulator having a heat resistance R2 smaller than the heat resistance R1 is used) in FIG. 10B.

When Rx is deleted by a combination of the equations (2) and (3), the following equation (4) can be obtained.

[Mathematical formula 1]

$$Tb = \frac{R2(Tt-Ta)Tt' - R1(Tt'-Ta')Tt}{R2(Tt-Ta) - R1(Tt'-Ta')} \quad (4)$$

Accordingly, in the sensor module of FIG. 10B, the core body temperature Tb can be calculated without being affected by an individual difference of the heat resistance Rx of the subcutaneous tissue.

PRIOR ART DOCUMENTS

Patent Documents

Patent Document 1: Japanese Unexamined Patent Publication No. 2002-372464
Patent Document 2: Japanese Unexamined Patent Publication No. 2007-212407

SUMMARY OF THE INVENTION

Problems to be Solved by the Invention

In the sensor modules in FIGS. 10A and 10B, information necessary for the calculation of the core body temperature Tb is obtained with plural temperature sensors. Because the temperature sensor does not have so high accuracy, the heat insulator having the high heat resistance and heat capacity is used in the sensor modules of FIGS. 10A and 10B. Therefore, the sensor modules has poor responsiveness (it takes a long time to obtain a stable measurement result of the core body temperature).

A temperature difference (hereinafter, referred to as a ΔT) corresponding to "Tt-Ta'" and a temperature difference (hereinafter, referred to as ΔT') corresponding to "Tt'-Ta'" can be obtained even in a device (hereinafter, referred to as a MEMS device or a MEMS chip) in which some thermopiles are incorporated using a MEMS technology.

When the MEMS device or MEMS chip is used to measure ΔT or ΔT and ΔT', the core body temperature can be measured with good responsiveness because a heat capacity largely decreases in a portion where the temperature difference is measured. On the other hand, because of a low voltage output from the thermopile of the MEMS device, there is a demand for a technology of increasing the temperature difference measured with the thermopile of the MEMS device.

One or more embodiments may provide a technology of increasing the temperature difference measured with the thermopile of the MEMS device.

Means for Solving the Problem

According to one or more embodiments, a temperature difference measuring apparatus includes: a bottomed tubular package in which a top face side is opened; a MEMS device disposed on an inner bottom face of the package, the MEMS device comprising at least one thermopile that measures a temperature difference, which is generated in the MEMS device by inflow heat through a bottom of the package; and a heat quantity increasing unit configured to increase a heat quantity flowing out from the MEMS device onto the top face side.

That is, the temperature difference measuring apparatus includes the heat quantity increasing unit that increases the heat quantity flowing out from the MEMS device onto the top face side. The temperature difference measured with the thermopile of the MEMS device is increased with increasing heat quantity flowing out from the MEMS device onto the top face (a surface on the opposite side to the bottom) side of the package. Accordingly, the use of the temperature difference measuring apparatus can make (produce) the internal temperature measuring apparatus or heat flux measuring apparatus in which the temperature difference measured with the thermopile of the MEMS device is increased, compared with the internal temperature measuring apparatus or heat flux measuring apparatus, including the same MEMS device while not including the heat quantity increasing unit.

Additionally, the temperature difference measuring apparatus has the configuration in which the MEMS device is disposed in the bottomed tubular package. Accordingly, compared with the case that the MEMS device is directly disposed on the printed wiring board, the use of the temperature difference measuring apparatus can produce the internal temperature measuring apparatus or heat flux measuring apparatus with ease (with a few number of processes necessary for the production).

In the temperature difference measuring apparatus, the bottomed tubular package in the top face side is opened may be a package having a shape such as a bottomed cylindrical shape, a bottomed elliptical tube shape, and a bottomed rectangular tube shape, and including a bottom and a sidewall surrounding a periphery of the bottom. Various structures can be adopted in the heat quantity increasing unit of the temperature difference measuring apparatus. For example, the temperature difference measuring apparatus may further include a top board covering a top face of the package as the heat quantity increasing unit, the top board being larger than the top face of the package, or the temperature difference measuring apparatus may further include a top board covering a top face of the package as the heat quantity increasing unit, the top board comprising at least one radiation fin. In the case that the above top board is used as the heat quantity increasing unit, because heat dissipation of the top board is improved, temperature at the top board is decreased. Resultantly, the temperature difference measured with the MEMS device (at least one thermopile of the MEMS device) is increased.

The temperature difference measuring apparatus may further include an infrared absorption member as the heat quantity increasing unit, the infrared absorption member being opposite to the MEMS device with a predetermined interval. The heat quantity increasing unit may adopt a structure including such the infrared absorption member and a top board in which the infrared absorption member is provided, the top board covering the opening of the package. The heat quantity increasing unit may also adopt a structure including such the infrared absorption member and a case in which the infrared absorption member is provided, the case covering the package such that a bottom of the package is exposed. When the above structures are adopted in the heat quantity increasing unit, heat transfer to the member (infrared absorption member, the top board in which the infrared absorption member is provided, and the case) located above the MEMS device is promoted, and therefore the temperature difference measured with the MEMS device is increased.

The heat quantity increasing unit with a top board may include a heat insulating member disposed between the top board and the top face of the package. When the above configuration is adopted, the temperature difference measured with the MEMS device is further increased because the temperature rise of the top board due to the heat passing through the sidewall of the package can be suppressed. In order to suppress temperature rise of the top board due to light incidence, in the temperature difference measuring apparatus, in the top board, a surface on a side that is not opposite to the package may be a light reflection surface.

The temperature difference measuring apparatus may further include a second MEMS device disposed on the inner bottom face of the package, the second MEMS device comprising at least one thermopile that measures a temperature difference, which is generated in the second MEMS device by inflow heat through the bottom of the package; a first top board, which is opposite to the MEMS device with a first interval, as the heat quantity increasing unit; and a second top board, which is opposite to the second MEMS device with a second interval larger than the first interval, as the heat quantity increasing unit.

When the above configuration is adopted, the temperature at the second top board can be lowered compared with the temperature at the first top board. Accordingly, the temperature difference measured with the MEMS chip located below the second top board can be increased.

Effect of the Invention

The use of the temperature difference measuring apparatus of one or more embodiments can easily construct the internal temperature measuring apparatus in which the temperature difference measured with the temperature difference of the MEMS device is increased.

MODE FOR CARRYING OUT THE INVENTION

Hereinafter, exemplary embodiments will be described with reference to the drawings.

First Embodiment

Figure 1:
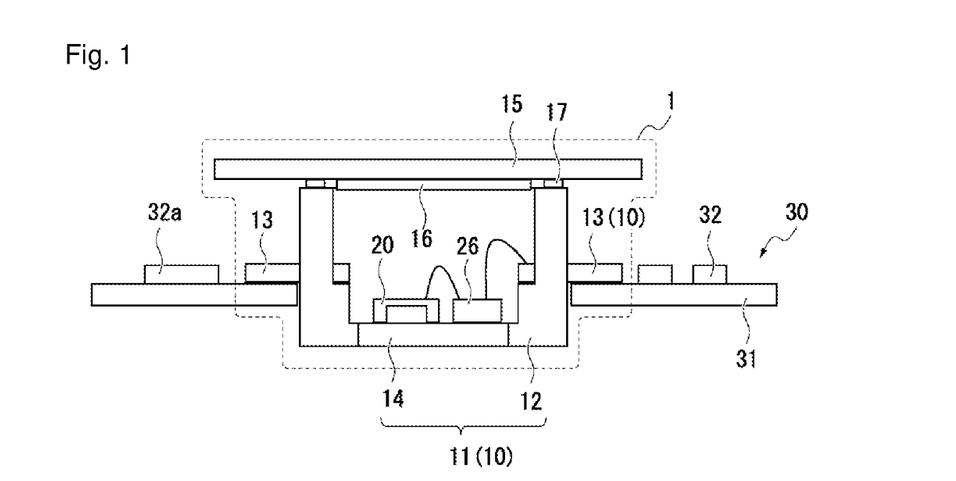
FIG. 1 is a schematic configuration diagram illustrating an internal temperature measuring apparatus provided with a temperature difference measuring apparatus according to a first embodiment.

FIG. 1 is a schematic configuration diagram illustrating an internal temperature measuring apparatus provided with a temperature difference measuring apparatus 1 according to a first embodiment.

The internal temperature measuring apparatus measures the internal temperature of a measurement object (such as a human body) in which a non-heating body exists near a surface. As illustrated in FIG. 1, the internal temperature measuring apparatus has a configuration in which the temperature difference measuring apparatus 1 is inserted in a through-hole made in a printed circuit board 30.

The printed circuit board 30 is a unit in which various devices 32 (for example, a resistor and a capacitor) such as an arithmetic circuit 32a are mounted on a printed wiring board 31. The arithmetic circuit 32a calculates the internal temperature of the measurement object from measurement results of a temperature difference and a temperature with the temperature difference measuring apparatus 1 (a MEMS chip 20 and an ASIC 26 (to be described later)), and outputs the internal temperature.

The through-hole in which the temperature difference measuring apparatus 1 is inserted is made in the printed wiring board 31 of the printed circuit board 30. In the sensor package 10, plural lands (not illustrated) are provided around the through-hole such that each land is opposite to the lead 13 inserted in the through-hole.

The temperature difference measuring apparatus 1 measures a value (a temperature and at least one temperature difference) necessary for the calculation of the internal temperature. As illustrated in FIG. 1, the temperature difference measuring apparatus 1 includes a sensor package 10 and a top board 15.

The sensor package 10 is a module in which the MEMS chip 20 and the ASIC 26 are disposed in a package 11 having a bottomed tubular shape including plural leads 13.

A configuration of the sensor package 10 will specifically be described below.

Figure 2:
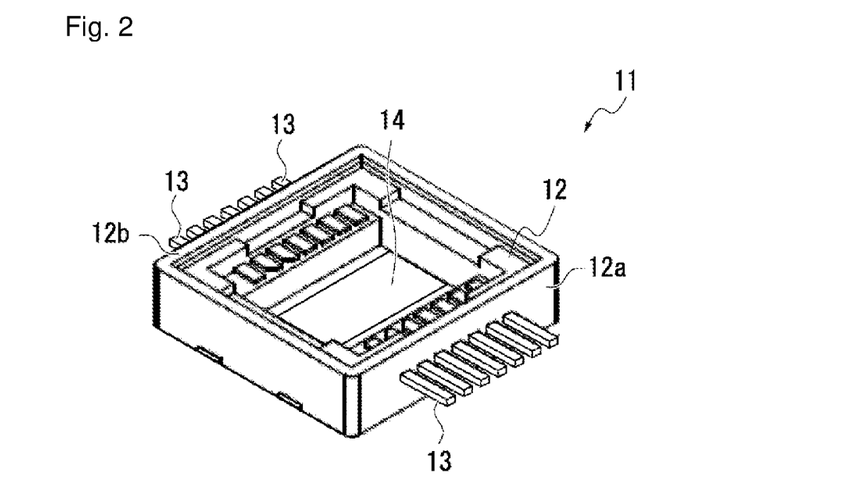
FIG. 2 is a perspective view illustrating a package included in a temperature difference measuring apparatus of a first embodiment.

FIG. 2 illustrates a configuration of the package 11. As illustrated in FIG. 2, the package 11 includes a casing 12 having a substantially bottomed square pipe shape and plural leads 13 piercing sidewalls 12a and 12b located opposite from each other in the casing 12. The interval between each lead 13 of the package 11 and the bottom face of the casing 12 is fixed such that the bottom face of the temperature difference measuring apparatus 1 projects from the bottom face of the printed circuit board 30 (printed wiring board 31) when the bottom side of the temperature difference measuring apparatus 1 (sensor package 10) is inserted in the through-hole of the printed circuit board 30 (see FIG. 1).

A heat transfer pad 14 is provided in the bottom of the casing 12 (hereinafter, also referred to as a casing bottom) of the package 11. The heat transfer pad 14 is made of a material (in a first embodiment, metal) having heat conductivity higher than that of a portion except for the heat transfer pad 14 of the casing bottom, and has the substantially same thickness as the portion except for the heat transfer pad 14 of the casing bottom. A constituent material of the portion except for the heat transfer pad 14 of the casing bottom and a constituent material of each sidewall of the casing 12 may be different from or identical to each other as long as the constituent materials have relatively poor heat conductivity. There is no particular limitation to a procedure to produce the package 11. However, the package 11 having the above configuration can easily be produced when mold forming (insert molding) is adopted. Accordingly, preferably the constituent material of the portion except for the heat transfer pad 14 of the casing 12 and the constituent material of each sidewall of the casing 12 are made of the same resin in order to be able to produce the package 11 by mold forming.

The MEMS chip 20 (see FIG. 1) is a compact temperature difference sensor (heat flux sensor), which is produced using a MEMS technology so as to include at least one thermopile that measures the temperature difference generated in the MEMS chip 20 by the in-flow heat flux through the casing bottom of the package 11.

A specific configuration of the MEMS chip 20 depends on the calculation method adopted to calculate the internal temperature. Specifically, as described in "BACKGROUND ART", the method for calculating the internal temperature includes the method in which the two temperature differences (Tt–Ta and Tt'–Ta') are required (see the equation (4)) and the method in which only one temperature difference is required (see the equation (1)).

The MEMS chip 20 including at least one thermopile that measures ΔT (the temperature difference corresponding to "Tt–Ta") and at least one thermopile that measures ΔT' (the temperature difference corresponding to "Tt'–Ta'") is used in the case that the former method is adopted to calculate the internal temperature. The MEMS chip 20 including at least one thermopile that measures ΔT (one kind of the temperature difference) is used in the case that the latter method is adopted to calculate the internal temperature.

A specific example (MEMS chips 20a and 20b) of the MEMS chip 20 will be described below with reference to FIGS. 3A, 3B, 4A, and 4B.

Figure 3A:
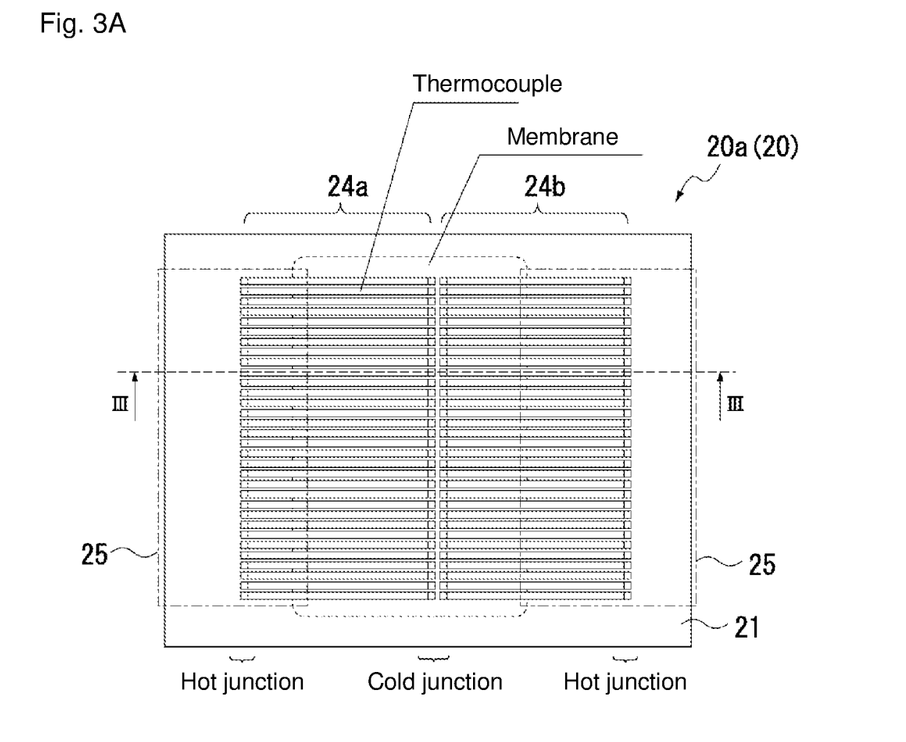
FIG. 3A is a plan view illustrating a MEMS chip including a thermopile that measures $\Delta T$ and a thermopile that measures $\Delta T'$.
Figure 3B:
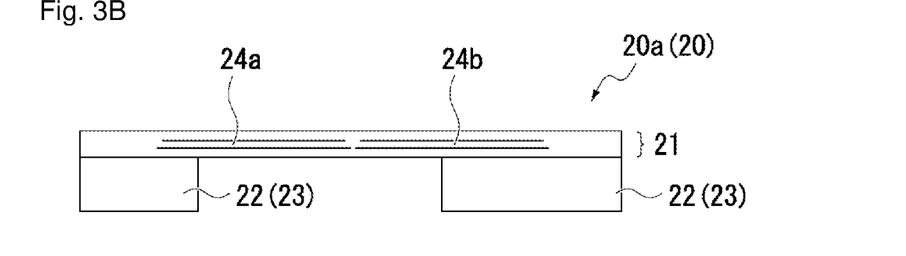
FIG. 3B is a sectional view taken on a line III-III of the MEMS chip in FIG. 3A.
Figure 4A:
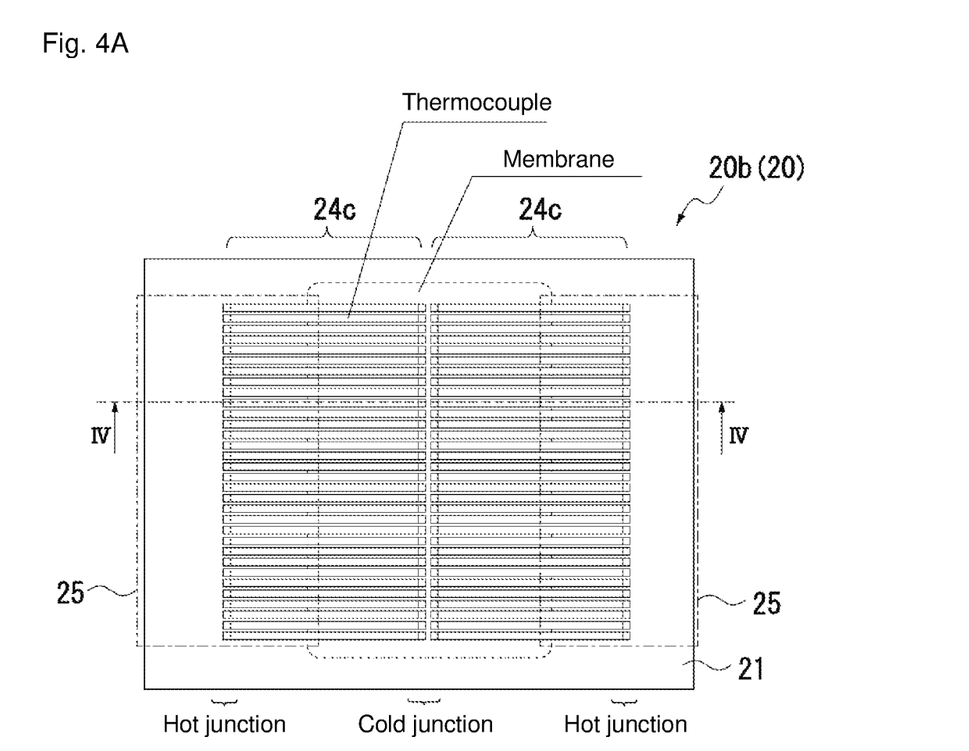
FIG. 4A is a plan view illustrating a MEMS chip not including a thermopile that measures $\Delta T'$.
Figure 4B:
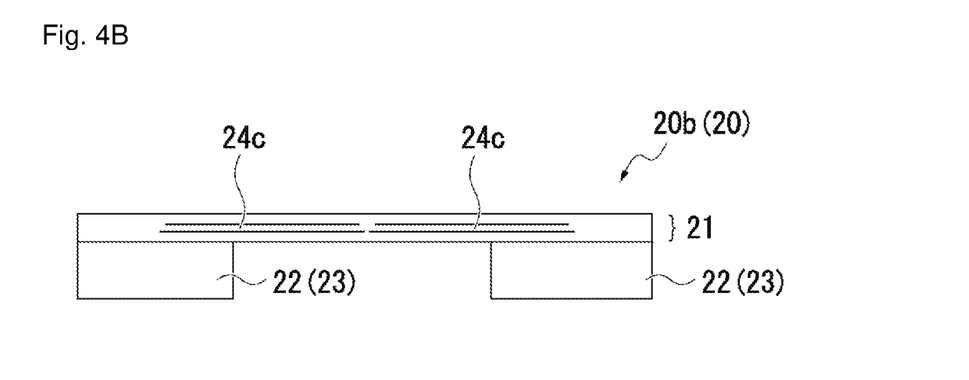
FIG. 4B is a sectional view taken on a line IV-IV of the MEMS chip in FIG. 4A.

FIG. 3A is a plan view illustrating the MEMS chip 20a including a thermopile 24a that measures ΔT and a thermopile 24b that measures ΔT'. FIG. 3B is a sectional view taken on a line III-III of the MEMS chip 20a in FIG. 3A. FIG. 4A is a plan view illustrating the MEMS chip 20b including two thermopiles 24c that measure ΔT (the MEMS chip 20b not including the thermopile 24 that measures ΔT'). FIG. 4B is a sectional view taken on a line IV-IV of the MEMS chip 20b in FIG. 4A.

As illustrated in FIGS. 3B and 4B, each MEMS chip 20 (20a and 20b) includes a top face 21 and a support 22. The top face 21 is formed on a silicon substrate using various semiconductor processes (such as film forming, resist pattern forming, and etching). The support 22 is formed by etching of the silicon substrate on which the top face 21 is formed from a backside.

As illustrated in FIGS. 3B and 4B, the support 22 of each MEMS chip 20 includes at least one cavity (etched portion) leading to the top face 21.

Hereinafter, in the top face 21, a portion located above the cavity of the support 22 is referred to as a membrane. In the support 22, a portion (in the top face 21, a portion of the support 22 located below the portion that becomes a temperature measurement target with a thermopile 24) in a frame 25 indicated by an alternate long and short dash line is referred to as a leg 23. The right and left in FIGS. 3A and 4B are simply referred to as the right and the left.

As illustrated in FIGS. 3A and 3B, thermopiles 24a and 24b in each of which plural thermocouples are connected in series are provided in the top face 21 of the MEMS chip 20a. Although not illustrated, an electrode is provided in an upper surface (the surface of the top side in FIGS. 3B and 4B) of the top face 21 of each MEMS chip 20 in order to take out output of each thermopile 24.

Each thermocouple constituting the thermopile 24a is substantially equal to each thermocouple constituting the thermopile 24b in a length. As illustrated in FIG. 3A, the hot junction and the cold junction of each thermocouple constituting the thermopile 24a are disposed on the leg 23 on the left of the MEMS chip 20a (in the support 22, the portion in the left frame 25 indicated by the alternate long and short dash line) and in a substantial center of a horizontal direction of the MEMS chip 20a in the membrane, respectively. The hot junction and the cold junction of each thermocouple constituting the thermopile 24b are disposed on the leg 23 on the right of the MEMS chip 20a and in the substantial center of the horizontal direction of the MEMS chip 20a in the membrane, respectively.

The center in the horizontal direction of the cavity included in the support 22 of the MEMS chip 20 is located on the left of the center in the horizontal direction of the MEMS chip 20. Resultantly, in the MEMS chip 20a, a heat resistance of a heat path from the bottom face of the left leg 23 to the portion in which the cold junction group of the thermopile 24a is provided in the top face 21 is larger than a heat resistance of a heat path from the bottom face of the right leg 23 to the portion in which the cold junction group of the thermopile 24b is provided in the top face 21.

Therefore, the MEMS chip 20a acts as a device in which the thermopile 24a measures the temperature difference $\Delta T$ while the thermopile 24b measures the temperature difference $\Delta T'$ ($<\Delta T$).

As is clear by comparison between FIGS. 4B and 3B, the MEMS chip 20b differs from the MEMS chip 20a in a position of the cavity. A center in a horizontal direction of the cavity of the MEMS chip 20b is matched with a center in the horizontal direction of the MEMS chip 20, so that the MEMS chip 20b can measure the same temperature difference $\Delta T$ using each thermopile 24c.

The sensor package 10 will still be described with reference to FIG. 1.

The ASIC 26 is an integrated circuit in which plural input and output electrodes are provided on the top surface of the integrated circuit. The ASIC 26 includes a temperature sensor. The ASIC 26 has a function of amplifying output of the temperature sensor and output of each thermopile 24 of the MEMS chip 20 and a function of digitizing each amplified output. For example, an integrated circuit including a proportional to absolute temperature (PTAT) voltage source that outputs voltage proportional to an absolute temperature (that is, a voltage source acting as a thermometer) can be used as the ASIC 26, a component of the PTAT voltage source acting as a temperature sensor.

The ASIC 26 and the MEMS chip 20 are disposed on the heat transfer pad 14 of the package 11 (casing 12). In the sensor package 10, the MEMS chip 20 and the ASIC 26 are electrically connected to each other by wire bonding, and the lead 13 and the ASIC 26 are electrically connected to each other by wire bonding.

A configuration of a portion except for the sensor package 10 in the temperature difference measuring apparatus 1 of a first embodiment will be described below.

As illustrated in FIG. 1, the temperature difference measuring apparatus 1 includes a heat insulating member 17 disposed on an upper end face of the sensor package 10, a top board 15 disposed on the heat insulating member 17, and an infrared absorption member 16 provided on the bottom face of the top board 15.

The heat insulating member 17 is made of a material (such as foamed plastic) having poor heat conductivity, and has a square annular shape in planar view. The heat insulating member 17 is disposed on the square annular upper end face (see FIG. 2) of the sensor package 10 so as to be able to surround the opening of the sensor package 10. The top board 15 is a plate-shaped member made of a material (such as metal and ceramic) having good heat conductivity. The top board 15 has a size larger than the top face of the sensor package 10, and is disposed on the heat insulating member 17 such that a center of the top board 15 is substantially matched with a center of the top face of the sensor package 10.

The infrared absorption member 16 is one having an infrared absorption function (such as a resin member containing antimony-dope tin oxide fine particles). As illustrated in FIG. 1, the infrared absorption member 16 is provided on the bottom face of the top board 15 and in a region opposite to the opening of the sensor package 10. The infrared absorption member 16 has a shape fitting in the opening of the sensor package 10.

As described above, the opening of the sensor package 10 of the temperature difference measuring apparatus 1 is covered with the top board 15 having the size larger than the top face of the sensor package 10, namely, the top board 15 having high heat dissipation. Therefore, the temperature rise of the top board 15 is suppressed in the temperature difference measuring apparatus 1. The heat insulating member 17 is provided between the top board 15 and the upper end face of the sensor package 10 in the temperature difference measuring apparatus 1. Accordingly, the temperature rise of the top board 15, which is caused by conduction of the heat passing through the sidewall of the sensor package 10 to the top board 15, is suppressed in the temperature difference measuring apparatus 1. The heat quantity flowing out upward from the MEMS chip 20 is increased when the top board 15 has a lower temperature. Therefore, in the above configuration, the temperature difference measured with each thermopile 24 can be increased compared with the case that the temperature rise of the top board 15 is not suppressed.

The infrared absorption member 16 opposite to the top face of the MEMS chip 20 is provided on the bottom face of the top board 15 of the temperature difference measuring apparatus 1. Therefore, in the temperature difference measuring apparatus 1, the infrared absorption member 16 promotes the heat transfer between the MEMS chip 20 and the top board 15, and the temperature difference measured with each thermopile 24 is increased.

Additionally, the temperature difference measuring apparatus 1 has the configuration in which the MEMS device is disposed in the bottomed tubular package. Accordingly, compared with the case that the MEMS device is directly disposed on the printed wiring board, the use of the temperature difference measuring apparatus 1 can produce the internal temperature measuring apparatus or heat flux measuring apparatus with ease (with a few number of processes necessary for the production).

Second Embodiment

A configuration of a temperature difference measuring apparatus according to a second embodiment will be described below while the description is focused on a difference from the temperature difference measuring apparatus 1 of a first embodiment.

Figure 5:
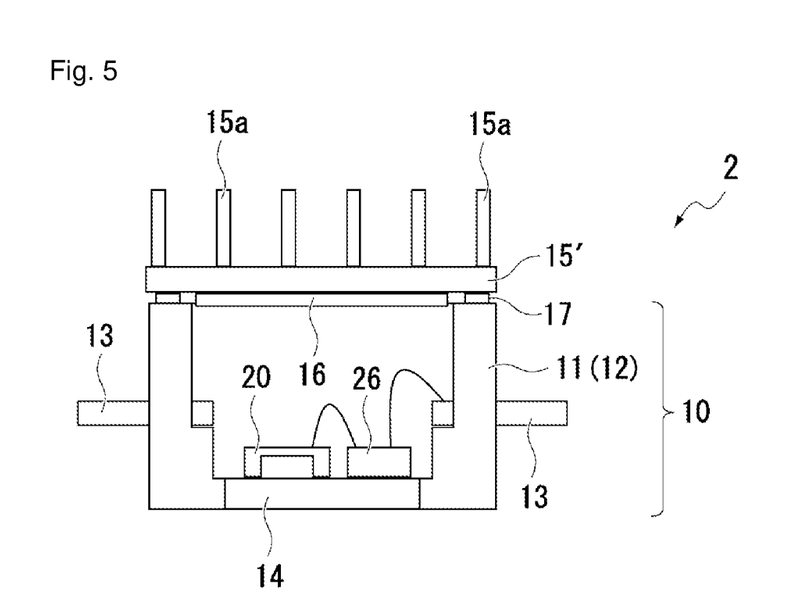
FIG. 5 is a schematic configuration diagram illustrating a temperature difference measuring apparatus according to a second embodiment.

FIG. 5 illustrates a schematic configuration of a temperature difference measuring apparatus 2 of a second embodiment. As is clear from comparison between FIGS. 5 and 1, in the temperature difference measuring apparatus 2, the top board 15 of the temperature difference measuring apparatus 1 is replaced with a top board 15' in which plural radiation fins 15a are provided on a plate-shaped member having the substantially same size as the top face of the sensor package 10.

The top board 15' having the above configuration has the high heat dissipation similarly to the top board 15, Accordingly, the configuration adopted in the temperature difference measuring apparatus 2 of a second embodiment can also increase the temperature difference measured with each thermopile 24 of the MEMS chip 20.

Third Embodiment

Figure 6:
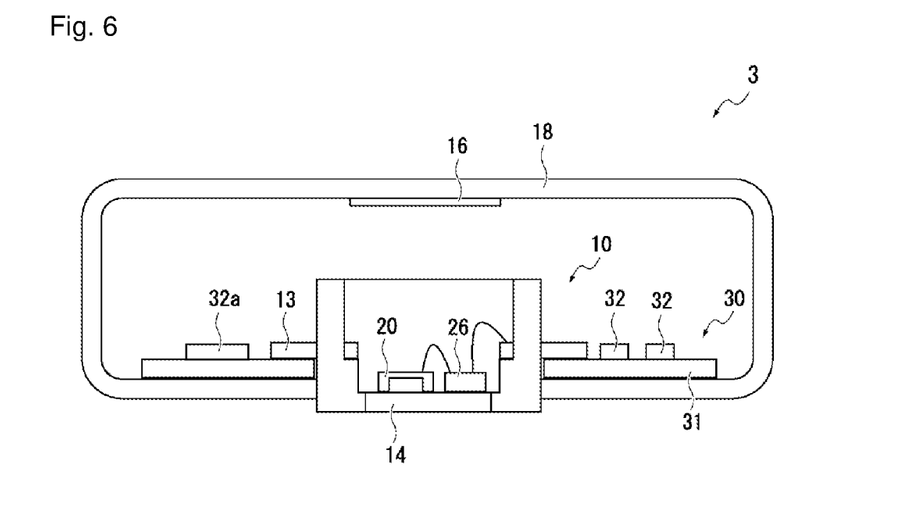
FIG. 6 is a schematic configuration diagram illustrating a temperature difference measuring apparatus according to a third embodiment.

FIG. 6 illustrates a schematic configuration of a temperature difference measuring apparatus 3 according to a third embodiment. A configuration of the temperature difference measuring apparatus 3 of a third embodiment will be described below with reference to FIG. 6 while the description is focused on a difference from the temperature difference measuring apparatus 1. Hereinafter, the top and bottom in FIG. 6 are simply referred to as a top and a bottom.

As illustrated in FIG. 6, the temperature difference measuring apparatus 3 includes a device in which the sensor package 10 is inserted in the through-hole of the printed circuit board 30, a case 18, and the infrared absorption member 16.

The printed circuit board 30 and sensor package 10 of the temperature difference measuring apparatus 3 are identical to the printed circuit board 30 and sensor package 10 of the temperature difference measuring apparatus 1. The infrared absorption member 16 of the temperature difference measuring apparatus 3 is identical to the infrared absorption member 16 of the temperature difference measuring apparatus 1. However, as illustrated in FIG. 6 the infrared absorption member 16 is provided on the bottom face of the case 18 and in the region opposite to the opening of the sensor package 10.

The case 18 has a shape in which the device, in which the sensor package 10 is inserted in the through-hole of the printed circuit board 30, can be accommodated while the bottom face of the sensor package 10 is exposed. The case 18 may be made of either a single material or plural kinds of materials. However, as is clear from FIG. 6, in the case 18, an upper-side portion acts as a member (a member corresponding to the top board 15) that emits heat to open air. Accordingly, in the case that the case 18 is made of a single material, preferably a material having good heat conductivity and good workability is used as a constituent material of the case 18. In the case that the case 18 is made of plural kinds of materials, preferably a material having good heat conductivity is used as a constituent material of the upper-side portion (for example, an upper half portion, or a portion in which the infrared absorption member 16 is provided and a peripheral portion thereof) of the case 18, and a material having poor heat conductivity is used as a constituent material of the remaining portion of the case 18.

As described above, the temperature difference measuring apparatus 3 of a third embodiment also includes the infrared absorption member 16 opposite to the top face of the MEMS chip 20 similarly to the temperature difference measuring apparatus 1. Accordingly, in the temperature difference measuring apparatus 3, the infrared absorption member 16 promotes the heat transfer between the MEMS chip 20 and the upper-side portion of the case 18, and the temperature difference measured with each thermopile 24 is increased.

Fourth Embodiment

Figure 7:
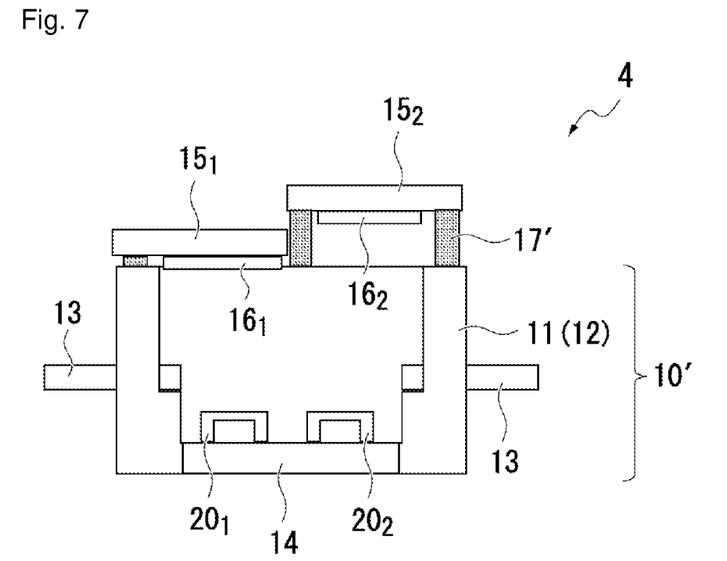
FIG. 7 is a schematic configuration diagram illustrating a temperature difference measuring apparatus according to a fourth embodiment n.

FIG. 7 illustrates a schematic configuration of a temperature difference measuring apparatus 4 according to a fourth embodiment. A configuration of the temperature difference measuring apparatus 4 of a fourth embodiment will be described below with reference to FIG. 7 while the description is focused on a difference from the temperature difference measuring apparatus 1.

The temperature difference measuring apparatus 4 is used as a component of the internal temperature measuring apparatus that measures the internal temperature using $\Delta T$ and $\Delta T'$. As described (defined) above, $\Delta T'$ means the temperature difference corresponding to "Tt'−Ta'" in the equation (4), and $\Delta T$ means the temperature difference corresponding to "Tt−Ta" in the equation (4).

As illustrated in FIG. 7, the temperature difference measuring apparatus 4 includes a sensor package 10', top boards $15_1$ and $15_2$, infrared absorption members $16_1$ and $16_2$, and a heat insulating member 17'.

In the sensor package 10', the MEMS chip 20 of the sensor package 10 (see FIG. 1) is replaced with MEMS chips $20_1$ and $20_2$. The MEMS chip $20_1$ and the MEMS chip $20_2$ measure $\Delta T'$ and $\Delta T$ ($>\Delta T'$), respectively. For example, a MEMS chip in which a length in the horizontal direction of the cavity is decreased shorter than the MEMS chip 20b (FIGS. 4A and 4B) and the MEMS chip 20b are used as the MEMS chips $20_1$ and $20_2$.

As illustrated in FIG. 7, the MEMS chip $20_1$ is disposed in a left region of two regions into which the bottom face of the sensor package 10' (package 11) is horizontally divided. The MEMS chip 202 is disposed in a right region.

Similarly to the top board 15, the top boards $15_1$ and $15_2$ are flat members made of a material having good heat conductivity. Similarly to the infrared absorption member 16, the infrared absorption members $16_1$ and $16_2$ are members having the infrared absorption function.

Similarly to the heat insulating member 17, the heat insulating member 17' (a hatched portion in FIG. 6) is provided to prevent the heat from being conducted to the top boards $15_1$ and $15_2$ through the sidewall of the package 11, and made of a material having poor heat conductivity. The heat insulating member 17' may be either a single member having a squarish eight shape in planar view or an assembly of plural members as long as the top boards $15_1$ and $15_2$ can be fixed at a position where an interval between the top board $15_2$ and the MEMS chip $20_2$ is larger than an interval between the top board 151 and the MEMS chip $20_1$.

The reason the above configuration is adopted in the temperature difference measuring apparatus 4 according to a fourth embodiment will be described below.

Preferably temperature at the top board (such as the top board 15) is matched with an ambient temperature. However, actually the temperature at the top board rises by the heat flowing in the temperature difference measuring apparatus from the measurement object through the bottom of the sensor package. When the above configuration is adopted, a temperature rise amount of the top board $15_2$ due to the heat from the measurement object is smaller than a temperature rise amount of the top board $15_1$. That is, the temperature at the top board $15_2$ is lower than the temperature at the top board $15_1$.

Therefore, the temperature difference $\Delta T$ measured with the MEMS chip $20_2$ located below the top board $15_2$ can be increased when the above configuration is adopted. In the case that the internal temperature is calculated using $\Delta T$ and $\Delta T'$, because the internal temperature can correctly be calculated when the value "$\Delta T - \Delta T'$" is increased, the above configuration is adopted in the temperature difference measuring apparatus 4.

Some supplements will be described below with respect to the temperature difference measuring apparatuses of first to fourth embodiments.

Various modifications can be made in each of the temperature difference measuring apparatuses of first to fourth embodiments. For example, the package 11 (casing 12) may be formed into the bottomed tubular shape, namely, the package 11 may include the bottom and the sidewall surrounding the periphery of the bottom. Accordingly, the package 11 (casing 12) may be formed into not the bottomed square tubular shape, but a bottomed rectangular tubular shape, bottomed cylindrical shape, a bottomed elliptical tubular shape, or the like. The temperature difference measuring apparatuses 1 to 3 of first to third embodiments can be modified into an apparatus used to measure a heat flux. The heat flux is a value, in which temperature is not used to calculate the heat flux.

Accordingly, in the case that the temperature difference measuring apparatuses of first to fourth embodiments are modified into the apparatus used to measure the heat flux, the temperature measuring function can be removed from the temperature difference measuring apparatus.

In order to prevent an increase in internal pressure caused by temperature rise of air in the temperature difference measuring apparatus, a member in which some grooves acting as an air inlet and an air outlet are formed in the top face and/or the bottom face or a member in which some through-holes acting as the air inlet and the air outlet are made may be used as the heat insulating member (17 and 17').

The temperature difference measuring apparatuses 1, 2, and 4 of first, second, and fourth embodiments may be modified into an apparatus (in other words, an apparatus in which the heat insulating members 17 and 17' are not used) in which the top board (15, $15_1$, and $15_2$) is directly fixed onto the sensor package (10 and 10'). For example, the temperature difference measuring apparatus 4 can be modified into an apparatus in which the top boards 151 and 152 are directly fixed onto the sensor package 10' by the use of the package 11 in which a step is provided in the top face. In the case that the temperature difference measuring apparatuses 1, 2, and 4 are modified into an apparatus (an apparatus in which the heat insulating member is not used) in which the top board is directly fixed onto the sensor package, instead of providing the groove in the heat insulating member, some grooves acting as the air inlet and the air outlet may be provided in the upper end face of the sensor package or the bottom face of the top board.

The top board in which the top face constitutes a light reflection surface reflecting light (in particular, infrared light) may be used in the temperature difference measuring apparatuses 1, 2, and 4. In this case, the temperature rise caused by the light incidence is suppressed in the top board. When the top board in which the top face constitutes the light reflection surface is used, the temperature difference measuring apparatuses 1, 2, and 4, which correctly measure the temperature difference even if the light is incident on the top board and in which the internal temperature is hardly increased during a heat treatment such as reflow, can be obtained. For example, the top board in which the top face constitutes the light reflection surface can be made by formation of the light reflection surface (light reflection layer) on a base such as a metallic plate.

In order to stabilize the air temperature in the apparatus, an inner surface of the temperature difference measuring apparatus (the package 11 and the casing 12) of each embodiment may be covered with a black material such as a black paint and a black resin.

In the case that the sensor package 10 is used to measure the core body temperature of the human body, an insulating film having biocompatibility or a resin member may be fixed to the bottom face of the sensor package 10. In order to improve thermal contact with the measurement object, the sensor package may be made such that the lower surface of the sensor package is formed into a curved shape in which a central portion is convex downward, or such that plural convex structures constructed with curved surfaces exist in the lower surface of the sensor package 10.

Figure 8:
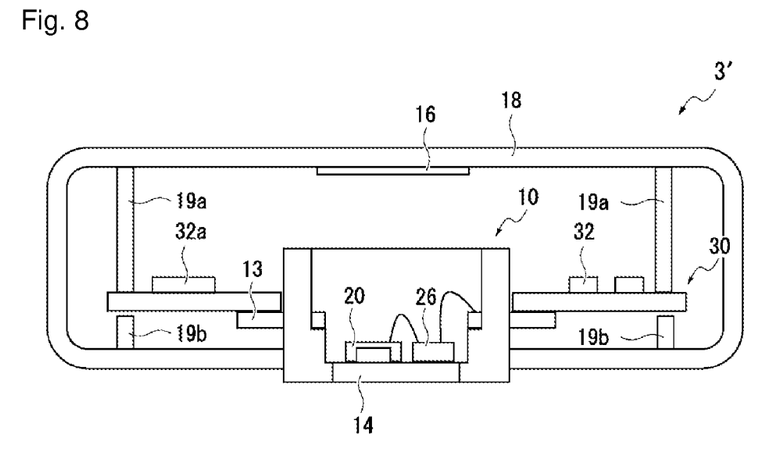
FIG. 8 is an explanatory view illustrating a modification of a temperature difference measuring apparatus of a third embodiment.

In the temperature difference measuring apparatus 3 (see FIG. 6), the heat can flow in the sensor package 10 from the measurement object through the case 18, the printed circuit board 30, and the lead 13. A measurement error is increased when the heat flows in the sensor package 10 through the lead 13. Therefore, in order to decrease a heat quantity flowing in the sensor package 10 through the lead 13, the temperature difference measuring apparatus 3 may be modified into a temperature difference measuring apparatus 3' having a configuration in FIG. 8.

That is, the temperature difference measuring apparatus 3 may be modified into a temperature difference measuring apparatus 3', which is fixed to the inner surface on the upper side of the case 18 using a member 19a such that the printed circuit board 30 is not separated from an inner bottom face of the case 18. A member 19b in FIG. 8 prevents the printed circuit board 30 from coming off from the member 19a, which is caused by deformation of the printed circuit board 30 and/or the case 18. The reason the member 19b is not fixed to the bottom face of the printed circuit board 30 is that the heat is prevented from flowing in the printed circuit board 30 from the case 18 through the member 19b.

In the casing bottom, the reason the heat transfer pad 14 having the high heat conductivity (see FIG. 1) is used as the portion where the MEMS chip 20 and the ASIC 26 are disposed is that in principle the temperature difference can correctly be measured for the good heat conductivity in a thickness direction of the casing bottom. However, in the case that the internal temperature is calculated from $\Delta T$ and $\Delta T'$, sometimes an estimated error (a difference between the calculation result of the internal temperature and the actual internal temperature) of the internal temperature increases because of the good heat conductivity in a crosswise direction (a direction perpendicular to the thickness direction) of the heat transfer pad 14. Accordingly, the casing bottom may be made of a material having relatively poor heat conductivity without providing the heat transfer pad 14 in the casing bottom.

Figure 9:
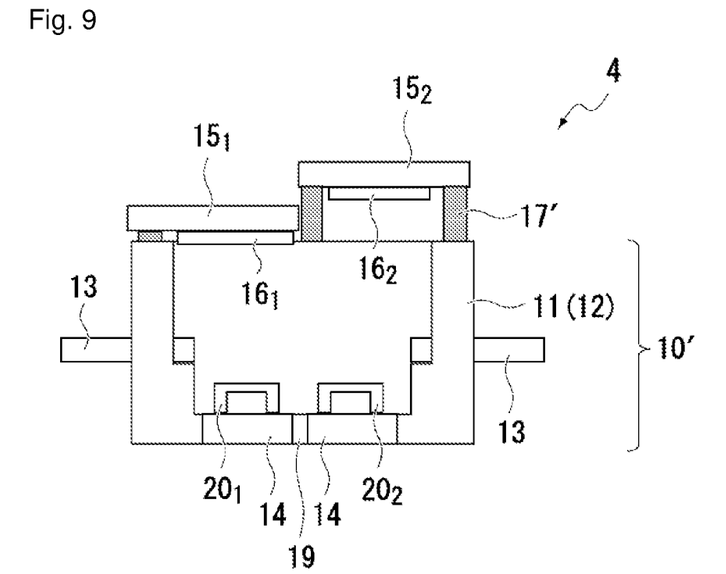
FIG. 9 is an explanatory view illustrating a modification of a temperature difference measuring apparatus of a fourth embodiment.

In order to prevent the increase in measurement error of the internal temperature due to the heat conduction in the crosswise direction of the casing bottom, in the temperature difference measuring apparatus in which MEMS chip 20 including the thermopile 24 for measuring the temperature difference $\Delta T$ and the thermopile 24 for measuring the temperature difference $\Delta T'$ is used, in order to prevent the estimated error of the internal temperature due to the heat conduction in the crosswise direction of the casing bottom, the heat transfer pads 14 are provided under the leg 23 on the hot junction side of the thermopile 24 for measuring the temperature difference $\Delta T$ of the MEMS chip 20 and the leg 23 on the hot junction side of the thermopile 24 for measuring the temperature difference $\Delta T'$, respectively, and the heat transfer pads 14 may be separated from each other using a poor heat conductive member. In the temperature difference measuring apparatus including the MEMS chip 20 for measuring the temperature difference $\Delta T$ and the MEMS chip 20 for measuring the temperature difference $\Delta T'$ such as the temperature difference measuring apparatus 4 (see FIG. 7), as illustrated in FIG. 9, the heat transfer pad 14 may be provided below each MEMS chip 20, and the heat transfer pads 14 may be separated from each other using a member 19 having poor heat conductivity.

DESCRIPTION OF SYMBOLS 1-4 temperature difference measuring apparatus
10 sensor package
11 package
12 casing
12a, 12b sidewall
13 lead
14 heat transfer pad
15 top board
18 case
20 MEMS chip
21 top face
22 support
23 leg
24, 24a, 24b, 24c thermopile
26 ASIC
30 printed circuit board
31 printed wiring board
32 device
32a arithmetic circuit

The invention claimed is:

1. A temperature difference measuring apparatus comprising: a bottomed tubular package in which a top face side is opened; a MEMS device disposed on an inner bottom face of the bottomed tubular package, the MEMS device comprising at least one thermopile that measures a temperature difference generated in the MEMS device by inflow heat through a bottom of the bottomed tubular package; and a heat quantity increasing unit configured to increase a heat quantity flowing out from the MEMS device onto the top face side.

2. The temperature difference measuring apparatus according to claim 1, further comprising a top board covering a top face of the bottomed tubular package as the heat quantity increasing unit, the top board being larger than the top face of the bottomed tubular package.

3. The temperature difference measuring apparatus according to claim 1, further comprising a top board covering a top face of the bottomed tubular package as the heat quantity increasing unit, the top board comprising at least one radiation fin.

4. The temperature difference measuring apparatus according to claim 1, further comprising an infrared absorption member as the heat quantity increasing unit, the infrared absorption member being opposite to the MEMS device at a predetermined interval.

5. The temperature difference measuring apparatus according to claim 4, wherein the heat quantity increasing unit comprises a top board in which the infrared absorption member is provided, the top board covering an opening of the bottomed tubular package.

6. The temperature difference measuring apparatus according to claim 4, wherein the heat quantity increasing unit comprises a case in which the infrared absorption member is provided, the case covering the bottomed tubular package such that the bottom of the bottomed tubular package is exposed.

7. The temperature difference measuring apparatus according to claim 2, wherein the heat quantity increasing unit comprises a heat insulating member disposed between the top board and the top face of the bottomed tubular package.

8. The temperature difference measuring apparatus according to claim 2, wherein, in the top board, a surface on a side that is not opposite to the bottomed tubular package comprises a light reflection surface.

9. The temperature difference measuring apparatus according to claim 1, further comprising a second MEMS device disposed on the inner bottom face of the bottomed tubular package, the second MEMS device comprising at least one thermopile that measures the temperature difference generated in the second MEMS device by the inflow heat through the bottom of the bottomed tubular package; a first top board opposite to the MEMS device at a first interval, as the heat quantity increasing unit; and a second top board opposite to the second MEMS device at a second interval larger than the first interval, as the heat quantity increasing unit.

* * * * *